(12) United States Patent
Bruszewski et al.

(10) Patent No.: US 8,540,764 B2
(45) Date of Patent: Sep. 24, 2013

(54) MOBILE EXTERNAL COUPLING FOR BRANCH VESSEL CONNECTION

(75) Inventors: Walter Bruszewski, Santa Rosa, CA (US); Peggy Grills, Hidden Valley Lake, CA (US); Frank Harewood, Ballybrit (IE); Lana Woolley, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 376 days.

(21) Appl. No.: 12/425,616

(22) Filed: Apr. 17, 2009

(65) Prior Publication Data
US 2010/0268327 A1  Oct. 21, 2010

(51) Int. Cl.
*A61F 2/06* (2013.01)

(52) U.S. Cl.
USPC .................. 623/1.35; 623/1.13; 623/1.16

(58) Field of Classification Search
None
See application file for complete search history.

(56) References Cited

U.S. PATENT DOCUMENTS

| | | | |
|---|---|---|---|
| 3,692,618 A | | 9/1972 | Dorschner et al. |
| 3,802,817 A | | 4/1974 | Matsuki et al. |
| 4,340,563 A | | 7/1982 | Appel et al. |
| 5,617,878 A | * | 4/1997 | Taheri ............... 128/898 |
| 5,800,514 A | | 9/1998 | Nunez et al. |
| 5,984,955 A | * | 11/1999 | Wisselink ............. 623/1.35 |
| 6,187,033 B1 | * | 2/2001 | Schmitt et al. ......... 623/1.35 |
| 6,248,097 B1 | | 6/2001 | Beitz et al. |
| 6,428,550 B1 | * | 8/2002 | Vargas et al. ........... 606/153 |
| 6,465,073 B1 | | 10/2002 | Morman et al. |
| 6,616,675 B1 | * | 9/2003 | Evard et al. ............ 606/155 |
| 6,645,242 B1 | * | 11/2003 | Quinn ................... 623/1.16 |
| 6,689,162 B1 | | 2/2004 | Thompson |
| 6,770,090 B2 | * | 8/2004 | Gantt et al. ............ 623/1.35 |
| 6,994,724 B2 | | 2/2006 | Schmitt |
| 7,189,257 B2 | | 3/2007 | Schmitt et al. |
| 7,264,632 B2 | | 9/2007 | Wright et al. |
| 7,407,509 B2 | * | 8/2008 | Greenberg et al. ...... 623/1.35 |
| 7,637,940 B2 | * | 12/2009 | Kocur et al. ........... 623/1.35 |
| 7,645,298 B2 | * | 1/2010 | Hartley et al. ......... 623/1.35 |
| 7,678,141 B2 | * | 3/2010 | Greenan et al. ........ 623/1.13 |
| 7,842,081 B2 | * | 11/2010 | Yadin ................... 623/1.35 |
| 8,128,686 B2 | * | 3/2012 | Paul et al. ............. 623/1.35 |
| 8,292,951 B2 | * | 10/2012 | Muzslay ............... 623/1.35 |
| 2002/0052648 A1 | * | 5/2002 | McGuckin et al. ...... 623/1.35 |
| 2003/0195609 A1 | | 10/2003 | Berenstein et al. |
| 2005/0102021 A1 | * | 5/2005 | Osborne ................ 623/1.13 |
| 2005/0149166 A1 | * | 7/2005 | Schaeffer et al. ...... 623/1.13 |

(Continued)

FOREIGN PATENT DOCUMENTS

| | | |
|---|---|---|
| EP | 0556749 | 2/1993 |
| EP | 1201212 | 5/2002 |

(Continued)

*Primary Examiner* — Thomas J Sweet
*Assistant Examiner* — Seema Mathew

(57) ABSTRACT

An endovascular prosthesis includes a tubular body and a mobile external coupling. The tubular body includes a graft material and stents coupled thereto, a forms a lumen therethrough. The mobile external coupling extends outwardly from the tubular body. The mobile external coupling includes a graft material and is generally frustoconically shaped. The mobile external coupling includes a base coupled to the tubular body, a top spaced from the tubular body, and a coupling lumen disposed between the base and the top, wherein the coupling lumen is in flow communication with the body lumen. The coupling graft material is a woven fabric with warp yarn which run generally parallel to a longitudinal axis of the mobile external coupling including a shape memory material.

24 Claims, 9 Drawing Sheets

(56) References Cited

U.S. PATENT DOCUMENTS

| | | |
|---|---|---|
| 2005/0222668 A1 | 10/2005 | Schaeffer et al. |
| 2005/0288775 A1* | 12/2005 | Dong ............................ 623/1.54 |
| 2006/0155359 A1* | 7/2006 | Watson ......................... 623/1.13 |
| 2006/0155362 A1 | 7/2006 | Israel |
| 2006/0247760 A1 | 11/2006 | Ganesan et al. |
| 2006/0247761 A1* | 11/2006 | Greenberg et al. ........... 623/1.16 |
| 2007/0118208 A1 | 5/2007 | Kerr |
| 2007/0135904 A1* | 6/2007 | Eidenschink et al. ........ 623/1.35 |
| 2007/0168013 A1* | 7/2007 | Douglas ........................ 623/1.12 |
| 2007/0208419 A1 | 9/2007 | Meyer et al. |
| 2007/0244542 A1* | 10/2007 | Greenan et al. .............. 623/1.13 |
| 2008/0114442 A1 | 5/2008 | Mitchell et al. |
| 2008/0262590 A1 | 10/2008 | Murray |
| 2009/0012596 A1 | 1/2009 | Kocur et al. |
| 2009/0030502 A1* | 1/2009 | Sun et al. ...................... 623/1.16 |
| 2009/0248135 A1 | 10/2009 | Bruszewski et al. |
| 2009/0264991 A1* | 10/2009 | Paul et al. ..................... 623/1.35 |
| 2010/0063576 A1* | 3/2010 | Schaeffer et al. ............. 623/1.13 |
| 2011/0208289 A1* | 8/2011 | Shalev .......................... 623/1.15 |
| 2011/0313512 A1* | 12/2011 | Hartley et al. ................ 623/1.35 |
| 2012/0123526 A1* | 5/2012 | Ko et al. ....................... 623/1.35 |
| 2012/0136431 A1* | 5/2012 | Chen ............................. 623/1.35 |
| 2012/0197383 A1* | 8/2012 | Ivancev et al. ............... 623/1.13 |

FOREIGN PATENT DOCUMENTS

| | | |
|---|---|---|
| EP | 1 847 236 | 10/2007 |
| EP | 1847234 | 10/2007 |
| EP | 1847237 | 10/2007 |
| WO | WO93/16669 | 9/1993 |
| WO | WO97/25002 | 7/1997 |
| WO | WO 97/25002 | 7/1997 |
| WO | WO02/067815 | 9/2002 |
| WO | WO 2005/032340 | 4/2005 |
| WO | WO2005/032340 | 4/2005 |
| WO | WO2005/034809 | 4/2005 |
| WO | WO2005/037160 | 4/2005 |
| WO | WO2006/113501 | 10/2006 |
| WO | WO2007/055768 | 5/2007 |
| WO | WO2010/024849 | 3/2010 |

* cited by examiner

FIG. 4
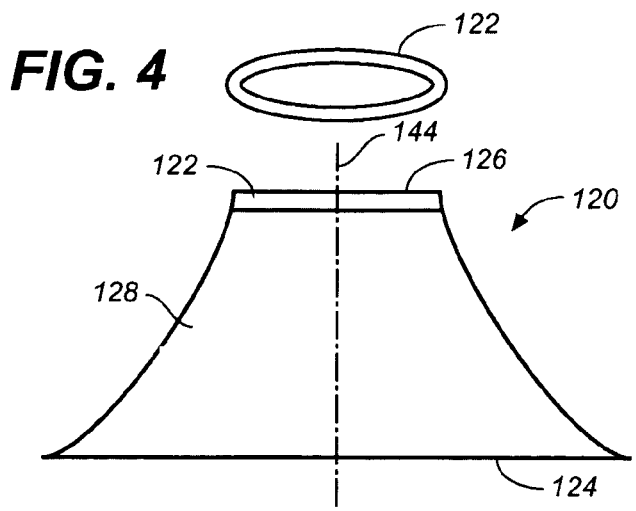
FIG. 3
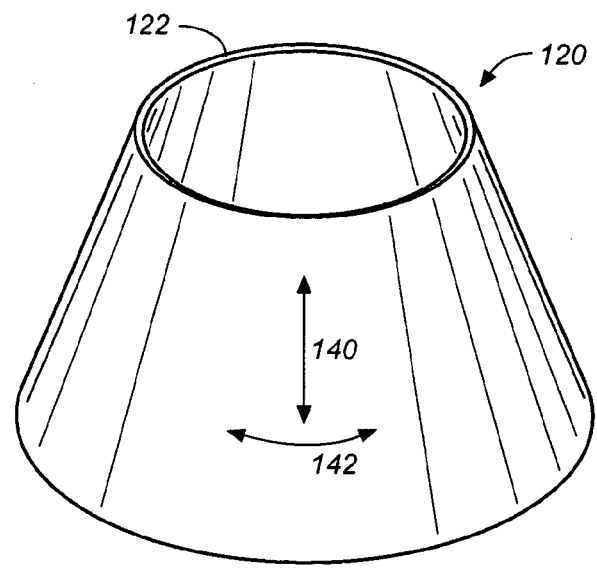
FIG. 5
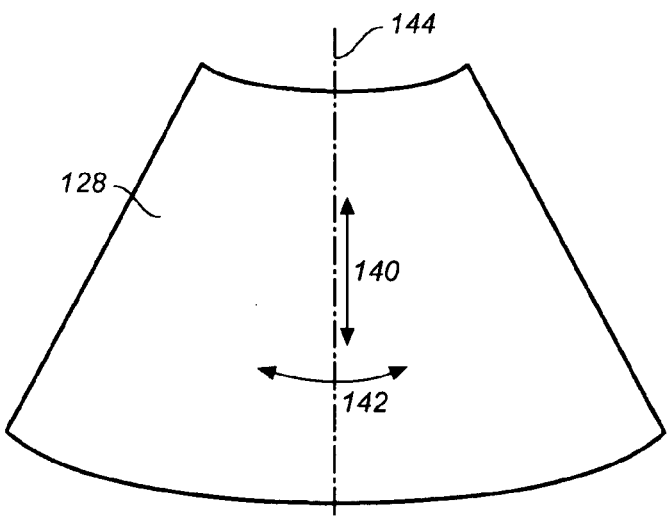
FIG. 6

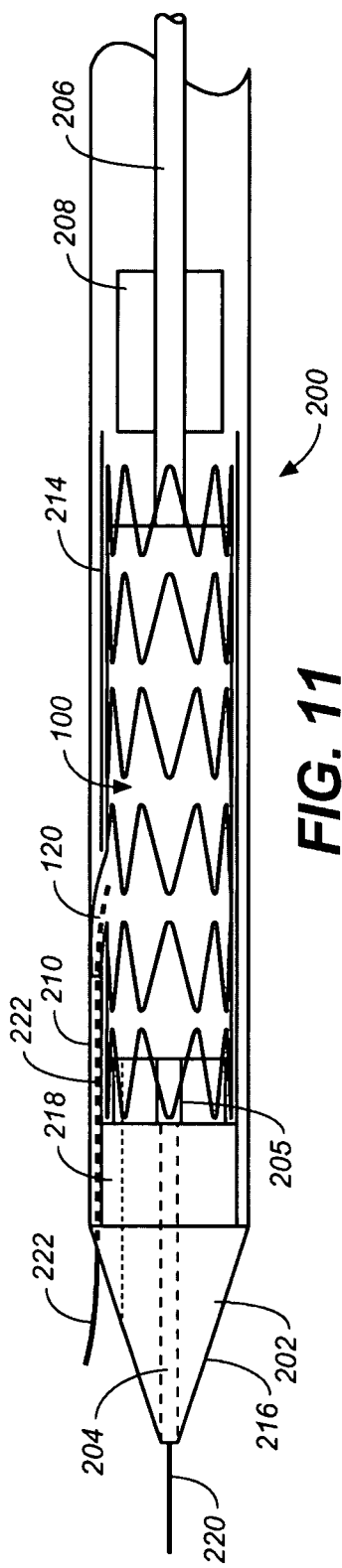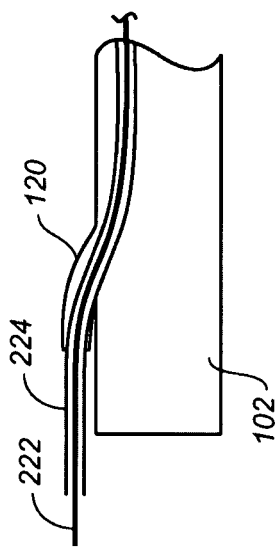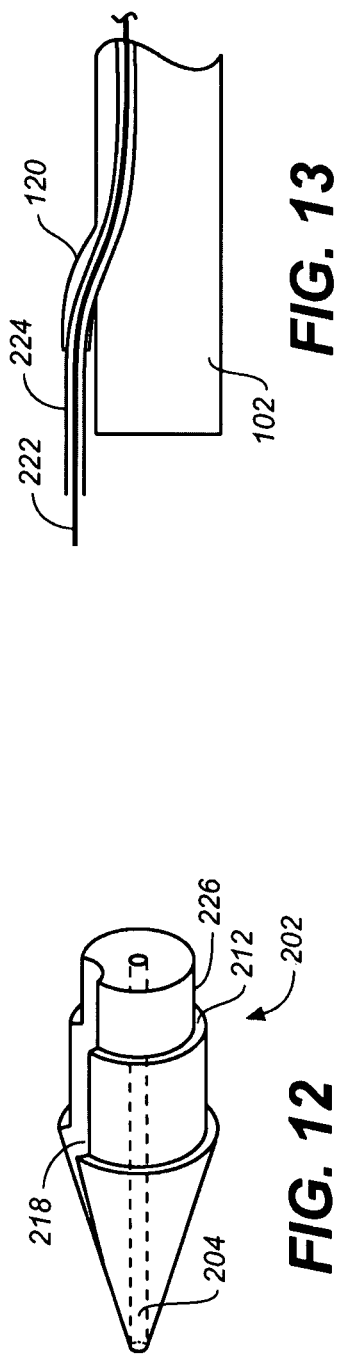
FIG. 11
FIG. 13
FIG. 12

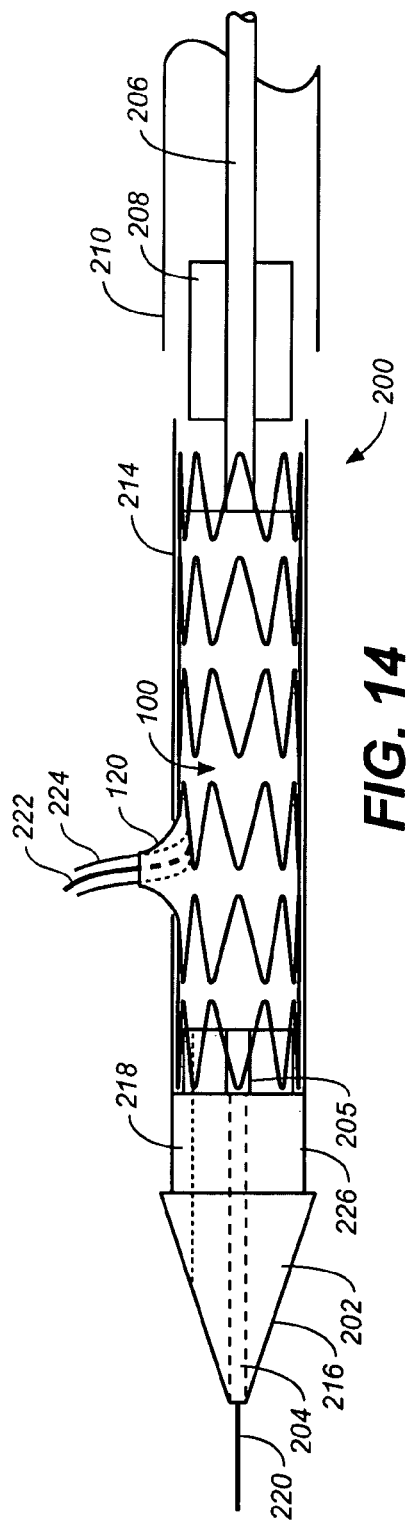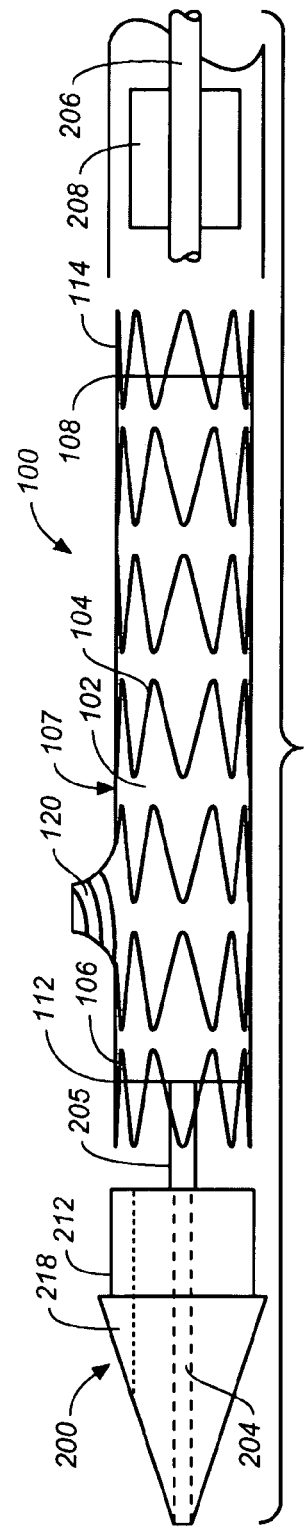
FIG. 14
FIG. 15

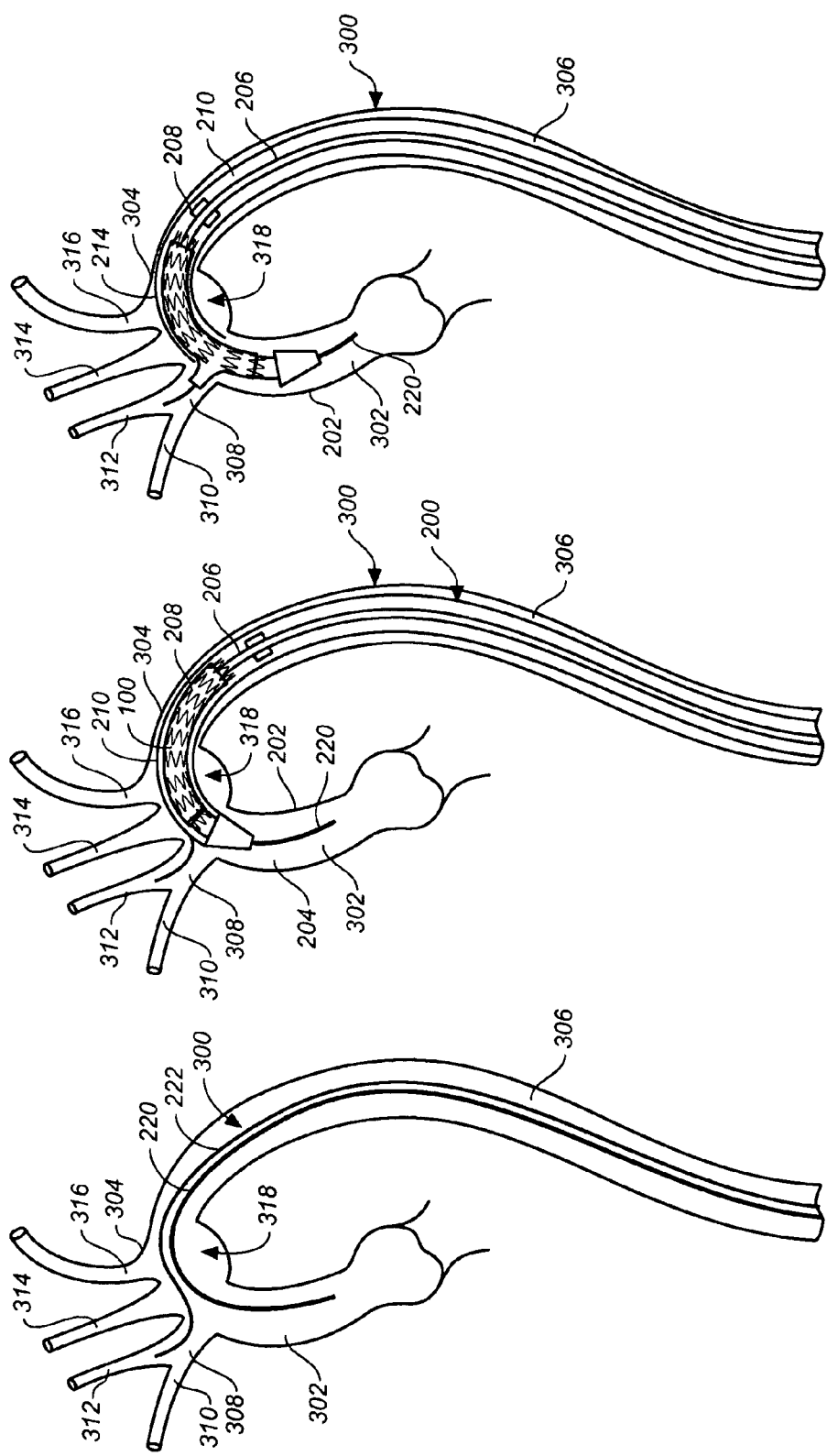

MOBILE EXTERNAL COUPLING FOR BRANCH VESSEL CONNECTION

FIELD OF THE INVENTION

This invention relates generally to endoluminal medical devices and procedures, and more particularly to an endoluminal prosthesis or graft having a mobile external coupling for connecting a main graft to a branch vessel graft.

BACKGROUND

Aneurysms and/or dissections may occur in blood vessels, and most typically occur in the aorta and peripheral arteries. Depending on the region of the aorta involved, the aneurysm may extend into areas having vessel bifurcations or segments of the aorta from which smaller "branch" arteries extend. Various types of aortic aneurysms may be classified on the basis of the region of aneurysmal involvement. For example, thoracic aortic aneurysms include aneurysms present in the ascending thoracic aorta, the aortic arch, and branch arteries that emanate therefrom, such as subclavian arteries, and also include aneurysms present in the descending thoracic aorta and branch arteries that emanate therefrom, such as thoracic intercostal arteries and/or the suprarenal abdominal aorta and branch arteries that emanate therefrom, which could include renal, superior mesenteric, celiac and/or intercostal arteries. Lastly, abdominal aortic aneurysms include aneurysms present in the aorta below the diaphragm, e.g., pararenal aorta and the branch arteries that emanate therefrom, such as the renal arteries.

The thoracic aorta has numerous arterial branches. The arch of the aorta has three major branches extending therefrom, all of which usually arise from the convex upper surface of the arch and ascend through the superior thoracic aperture. The brachiocephalic artery originates anterior to the trachea. The brachiocephalic artery divides into two branches, the right subclavian artery (which supplies blood to the right arm) and the right common carotid artery (which supplies blood to the right side of the head and neck). The left common carotid artery arises from the arch of the aorta just to the left of the origin of the brachiocephalic artery. The left common carotid artery supplies blood to the left side of the head and neck. The third branch arising from the aortic arch, the left subclavian artery, originates behind and just to the left of the origin of the left common carotid artery and supplies blood to the left arm.

For patients with thoracic aneurysms of the aortic arch, surgery to replace the aorta may be performed where the aorta is replaced with a fabric substitute in an operation that uses a heart-lung machine. In such a case, the aneurysmal portion of the aorta is removed or opened and a substitute lumen is sewn across the aneurysmal portion. Such surgery is highly invasive, requires an extended recovery period and, therefore, cannot be performed on individuals in fragile health or with other contraindicative factors.

Alternatively, the aneurysmal region of the aorta can be bypassed by use of a tubular exclusion device, e.g., by a stent-graft placed inside the vessel spanning the aneurysmal portion of the vessel, to seal off the aneurysmal portion from further exposure to blood flowing through the aorta. A stent-graft can be implanted without a chest incision, using specialized catheters that are introduced through arteries, usually through incisions in the groin region of the patient. The use of stent-grafts to internally bypass, within the aorta or flow lumen, the aneurysmal site, is also not without issues. In particular, where a stent-graft is used in a thoracic location, care must be taken so that critical branch arteries are not covered or occluded by the stent-graft yet the stent-graft must seal against the aorta wall and provide a flow conduit for blood to flow past the aneurysmal site. Where the aneurysm is located immediately adjacent to the branch arteries, there is a need to deploy the stent-graft in a location which partially or fully extends across the location of the origin of the branch arteries from the aorta to ensure sealing of the stent-graft to the artery wall.

To accommodate side branches, main vessel stent-grafts having a fenestration or opening in a side wall thereof may be utilized. The main vessel stent graft is positioned to align the fenestration with the ostium of the branch vessel after deployment. In use, a proximal end of the stent-graft, having one or more side openings, is prepositioned and securely anchored in place so that the fenestrations or openings are oriented when deployed to avoid blocking or restricting blood flow into the side branches. Fenestrations by themselves do not form a tight seal or include discrete conduit(s) through which blood can be channeled into the adjacent side branch artery. As a result, blood leakage is prone to occur into the space between the outer surface of the aortic graft and the surrounding aortic wall between the edges of the graft surrounding the fenestrations and the adjacent vessel wall. Similar blood leakage can result from post-implantation migration or movement of the stent-graft causing misalignment of the fenestration(s) and the branch artery(ies), which may also result in impaired flow into the branch artery(ies).

In some cases, the main vessel stent graft is supplemented by another stent-graft, often referred to as a branch stent-graft. The branch graft is deployed through the fenestration into the branch vessel to provide a conduit for blood flow into the branch vessel. The branch stent-graft is preferably sealingly connected to the main graft in situ to prevent undesired leakage. This connection between the branch graft and main graft may be difficult to create effectively in situ and is a site for potential leakage.

In some instances, branch graft extensions (stent-grafts) are incorporated into the main stent-graft. Such branch graft extensions are folded or collapsed against the main stent-graft for delivery and require complicated procedures, requiring multiple sleeves and guidewires, to direct the branch extension into the branch vessel and subsequently expand. Further, in some instances, such branch stent-grafts tend to return to their folded or collapsed configuration, and thus do not provide an unobstructed flow path to the branch vessel.

Thus, there remains a need in the art for improvements in stent graft structures for directing flow from a main vessel, such as the aorta, into branch vessels emanating therefrom, such as branch vessels of the aortic arch.

SUMMARY OF THE INVENTION

An embodiment of an endovascular prosthesis includes a tubular body and a mobile external coupling. The tubular body includes a graft material and stents coupled thereto, and forms a lumen therethrough. The mobile external coupling extends outwardly from the tubular body. The mobile external coupling includes a graft material and is generally frustoconically shaped. The mobile external coupling includes a base coupled to the tubular body, a top spaced from the tubular body, and a coupling body forming a coupling lumen therein disposed between the base and the top, wherein the coupling lumen is in flow communication with the body lumen. The coupling graft material is a woven fabric with warp yarns that include a shape memory material. The shape memory material is shape set to be straight such that the mobile external coupling when released into a relaxed (unconstrained state) is urged away from the tubular body.

In a method for delivering and deploying the endovascular prosthesis a main prosthesis is delivered in a compressed configuration to a target location in a main vessel such that the mobile external coupling is generally aligned with a branch vessel. A sleeve is retracted to expose the mobile external coupling. Minor adjustments to the location of the main body may be needed to locate the mobile external coupling to better align it with the branch vessel may be necessary. The tubular body is deployed such that it expands from the compressed configuration to an expanded configuration. A branch vessel prosthesis may be delivered in a compressed configuration to the branch vessel. The branch vessel prosthesis may be deployed such that the branch vessel prosthesis radially expands to an expanded configuration and an outside surface of a portion of the branch vessel prosthesis is in contact with an inner surface of a portion of the mobile external coupling.

BRIEF DESCRIPTION OF DRAWINGS

The foregoing and other features and advantages of embodiments according to the invention will be apparent from the following description as illustrated in the accompanying drawings. The accompanying drawings, which are incorporated herein and form a part of the specification, further serve to explain the principles of the embodiments and to enable a person skilled in the pertinent art to make and use the described embodiments herein. The drawings are not to scale.

FIG. 3 is a schematic illustration of the stent portion of the mobile external coupling of the stent-graft of FIG. 1.

FIG. 4 is a schematic illustration of a stent ring disposed at the top of the mobile external coupling of the stent-graft of FIG. 1.

FIG. 5 is a schematic illustration of the mobile external coupling of the stent-graft of FIG. 1.

FIG. 6 is a front view of a sheet of material used in a method of making the mobile external coupling of the stent-graft of FIG. 1.

FIG. 11 is a schematic illustration of a stent-graft delivery device.

FIG. 12 is a schematic perspective view of the tip of the stent-graft delivery device of FIG. 11.

FIG. 13 is a schematic illustration of a portion of the stent-graft and a portion of the stent-graft delivery device.

FIGS. 14 and 15 are schematic illustrations illustrating progressive steps of the stent-graft delivery device of FIG. 11 as the sheath is retracted.

FIGS. 16-21 are schematic illustrations of progressive steps a method for delivering and deploying the stent-graft of FIG. 1 and a branch stent-graft to a target location.

DETAILED DESCRIPTION

Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent graft device "proximal" is the portion nearer the heart by way of blood flow path while "distal" is the portion of the stent graft further from the heart by way of blood flow path.

Figure 1:
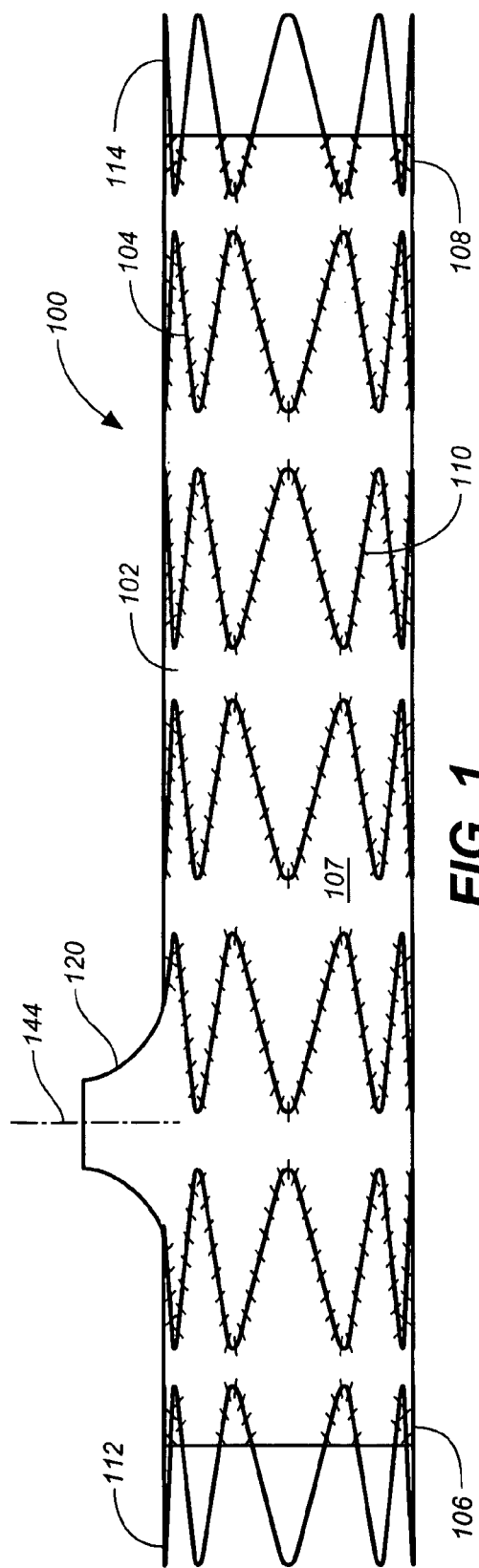
FIG. 1 is a schematic side view of an endoluminal stent-graft according to an embodiment hereof.
Figure 2:
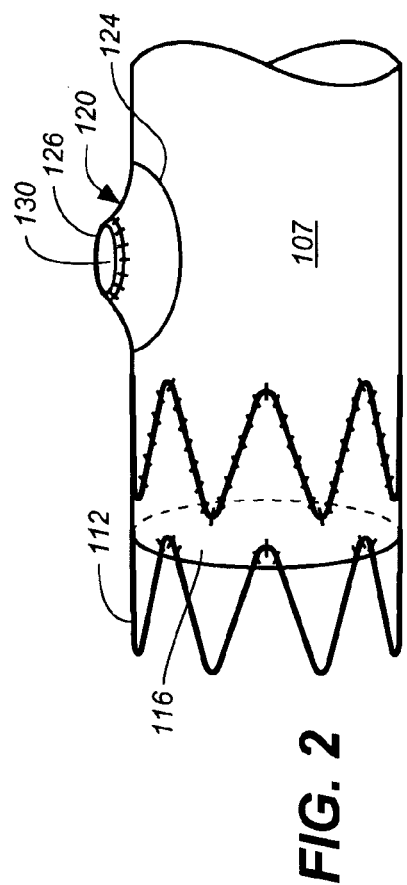
FIG. 2 is a schematic close up illustration of a portion of the stent-graft of FIG. 1.

With reference to FIGS. 1-3, a stent-graft 100 is configured for placement in a vessel such as the aorta. Stent-graft 100 includes graft material 102 coupled to stents 104. Graft material 102 may be coupled to stents 104 using stitching 110 or other means known to those of skill in the art. In the embodiment shown in FIGS. 1-3 stents 104 are coupled to an outside surface of graft material 102. However, stents 104 may alternatively be coupled to an inside surface of graft material 102. Graft material 102 may be any suitable graft material, for example and not limited to, woven polyester, DACRON® material, expanded polytetrafluoroethylene, polyurethane, silicone, or other suitable materials. Stents 104 may be any conventional stent material or configuration. As shown, stents 104 are preferably made from a shape memory material, such as thermally treated stainless steel or nickel-titanium alloy (nitinol), and are formed into a zig-zag configuration. Stent-graft 100 includes a proximal end 106, a distal end 108, and a body 107 therebetween. Proximal stent 112 and distal stent 114 may extend outside of the graft material 102, as shown, and may also be generally described as anchor stents or crown stents in the art. Body 107 has a lumen 116 disposed therethrough. Stent-graft 100 further includes a mobile external coupling 120, described in detail below. Except for the mobile external coupling 120, stent graft-100 may be similar to the Medtronic, Inc.'s VALIANT® thoracic stent-graft, or other known stent-grafts.

Mobile external coupling 120 is disposed on an outside surface of stent-graft 100 at an opening in graft material 102. Mobile external coupling 120 is generally frustoconically shaped. Mobile external coupling 120 includes a base 124, top 126, and graft material 128. A wire 122 shaped as a circle may be disposed at top 126, for example by folding graft material 128 over wire 122 and stitching the folded over portion of the graft material 128 to itself. Although mobile external coupling 120 is described as generally frustoconical in shape, base 124 is preferably generally elliptical rather than circular. Base 124 may have, for example and not by way of limitation, a long axis of approximately 20-30 mm and a short axis of approximately 15-20 mm. Further, the height of mobile external coupling 120 may be approximately 10-15 mm. Further, the diameter of the top 126 of mobile external coupling may be approximately 8-12 mm if it is to be used at the junction of the aorta and left common carotid artery, the junction of the aorta and left subclavian artery, or the junction of the aorta and the brachiocephalic artery.

Graft material 128 of mobile external coupling 120 is a woven medical textile that is formed through the process of interlacing two yarns of material so that they cross each other at right angles, which produces a woven fabric. The warp yarns of graft material 128 run lengthwise, that is, when the inclined threads of the yarn of the conical surface are projected to the longitudinal axis 144 they are generally parallel to the longitudinal axis 144 of mobile external coupling 120. The fill yarn is interlaced in a transverse relation between the warp yarns. Thus, as shown in FIG. 5, the warp yarns of graft material 128 are in the direction of arrow(s) 140 and the fill yarns are in the direction of arrow(s) 142. The warp yarns for mobile external coupling 120 are composite yarns made from combination of a thermoplastic yarns and a shape memory material. Thermoplastic yarns suitable for use in graft material 128 include, but are not limited to, polyesters, polypropylenes, polyethylenes (such as polyethylene terephthalate (PET)), polyurethanes, polytetrafluoroethylenes, and mixtures thereof. A preferred material for the thermoplastic yarn is polyethylene terephthalate. The shape memory material is preferably nitinol, but may be other shape memory materials. The fill yarn may be any of the thermoplastic yarns listed above, preferably polyethylene terephthalate (PET). The shape memory material of the warp yarns is shape set straight and thus in the collective frustoconical structure urges mobile external coupling 120 to protrude away from the body 107. Thus, when mobile external coupling 120 is released from its delivery configuration, as explained in more detail below, mobile external coupling 120 will self (expand) configure to extend away from body 107.

Mobile external coupling 120 allows for significant flexibility in aligning stent-graft 100 with a branch vessel because the top of the mobile external coupling 120 can move. This mobility is due to the shape of mobile external coupling 120 and can be further improved by utilizing some excess graft material 128 when forming mobile external coupling 120. Thus, if stent-graft 100 is not perfectly aligned with a branch vessel, the top 126 of mobile external coupling 120 can move or shift such that mobile external coupling 120 will extend into the branch vessel. Further, due to the composition of graft material 128 explained above, mobile external coupling 120 pops out from body 107 of stent-graft 100 when released from a sleeve during delivery to a target site. This prevents bunching or collapse of the mobile external coupling 120 when released from the delivery system.

Figure 7:
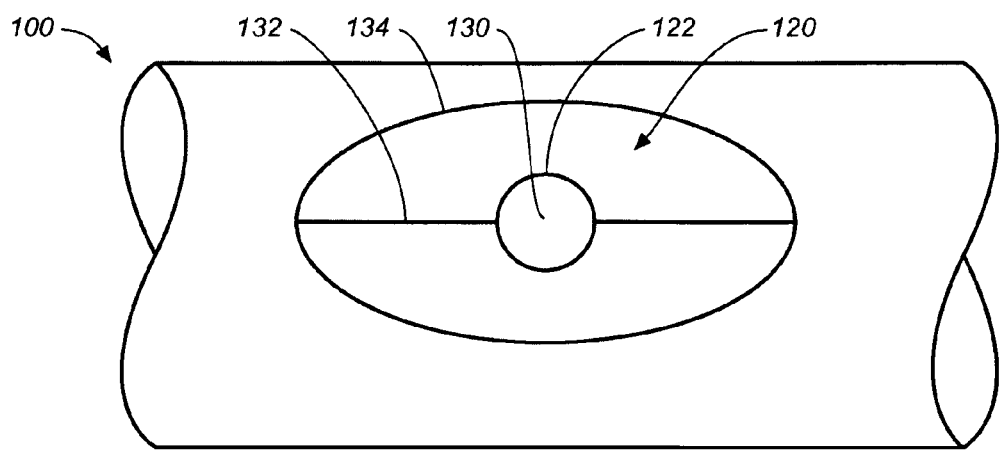
FIG. 7 is a top view of the mobile external coupling of the stent-graft of FIG. 1 made according to a method hereof.

Mobile external coupling 120 with the shape memory material woven as discussed above can be formed in many ways. In an embodiment, two sheets of graft material 128 as shown in FIG. 6 are formed by weaving thermoplastic/shape memory composite yarns in direction 140 and a thermoplastic yarn in direction 142. The two sheets are sewn or otherwise attached together in the shape of mobile external coupling 120 and then sewn or otherwise attached to graft material 102 of body 107. In such an embodiment, seams 132 are formed where the two sheets are attached to each other and seam 134 is formed where mobile external coupling 120 is coupled to graft material 102 of body 107, as shown in FIG. 7.

Figure 8:
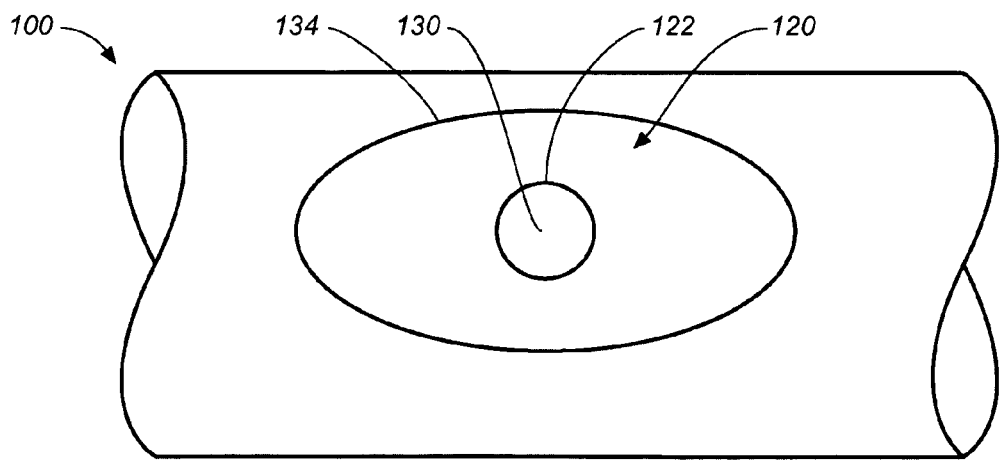
FIG. 8 is a top view of the mobile external coupling of the stent-graft of FIG. 1 made according to another method hereof.

In another embodiment for forming mobile external coupling 120, mobile external coupling 120 is formed as a unitary body with thermoplastic/shape memory composite yarns in direction 140 and a thermoplastic yarn in direction 142. Such a unitary body can be formed in the generally frustoconical shape of mobile external coupling 120 by the methods, for example, disclosed in U.S. Pat. No. 5,800,514, U.S. Pat. No. 6,994,724, and U.S. Pat. No. 7,189,257, the disclosures of which are incorporated by reference herein in their entirety. More particularly, by disengaging and/or engaging selected warp yarns, gradual changes in size, shape or configuration of the graft material, such as diameter change of a frustoconical shape, can be accomplished during weaving of the graft. A mobile external coupling 120 formed as a unitary body can then be sewn or otherwise attached to graft materials 102 of body 107, creating a seam 134, as shown in FIG. 8. However, conically oriented seams 132, as in the embodiment shown in FIG. 7, are avoided.

Figure 9:
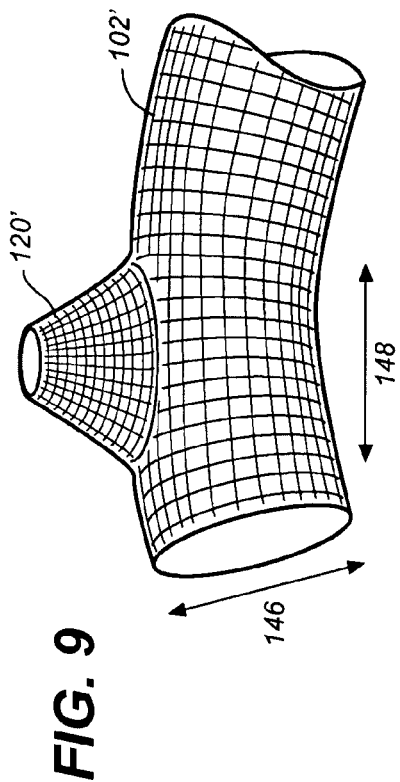
FIG. 9 is a schematic illustration of a portion of the stent-graft of FIG. 1 made according to another method hereof.

In another embodiment, graft material 128 of mobile external coupling 120' can be weaved as a unitary body with graft material 102' of body (e.g., 107), as shown in FIG. 9. Thermoplastics thermoplastic/shape memory composite yarns are weaved in direction 146 and thermoplastic yarns are weaved in direction 148. Thus, mobile external coupling 120' will tend to protrude away from body (e.g., 107), as discussed above, due to the presence of the shape memory material in direct 146. Further, due to the shape memory material in the graft material 102' of the body, graft material 102' will tend to remain in its tubular form and resist compressive forces from the vessel in which it is installed. Although not shown in FIG. 9, stents (e.g., 104) may still be attached to graft material 102', as shown in the previous figures. The unitary construction of graft material 102' of body (e.g., 107) and graft material 128 of mobile external coupling 120' can be accomplished by the methods, for example, disclosed in U.S. Pat. No. 5,800,514, U.S. Pat. No. 6,994,724, and U.S. Pat. No. 7,189,257, the disclosures of which are incorporated by reference herein in their entirety.

Figure 10:
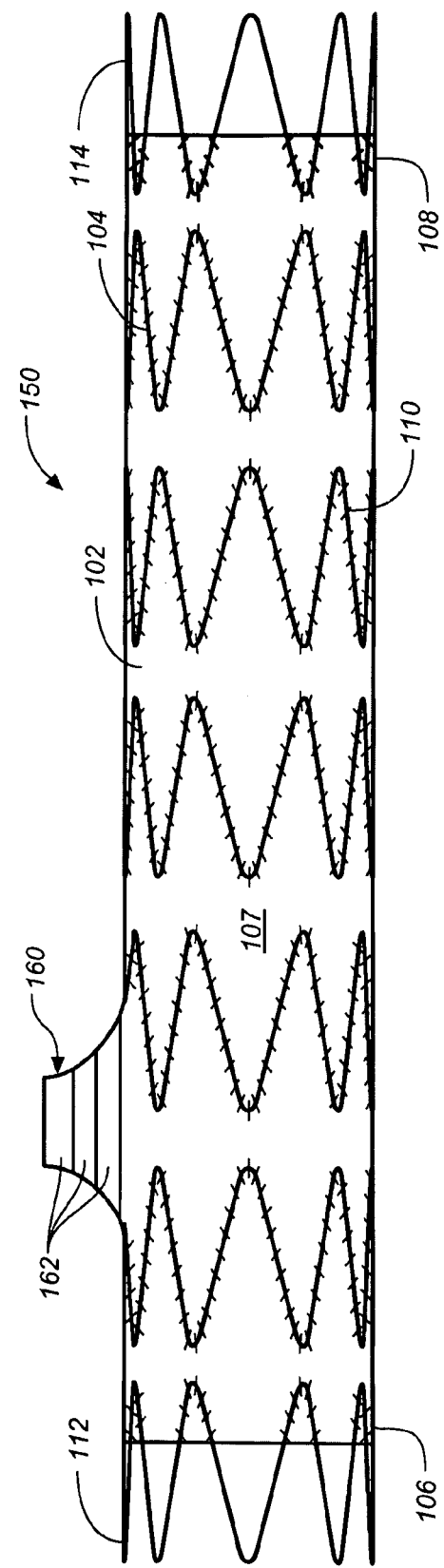
FIG. 10 is a schematic side view of an endoluminal stent-graft according to another embodiment hereof.

FIG. 10 shows a stent-graft 150 in accordance with another embodiment hereof. Stent-graft 150 is similar to stent-graft 100 of FIG. 1 and similar features are accordingly given the same reference numerals. Stent-graft 150 includes a mobile external coupling 160 that is made of bands 162 of elasticated material collectively forming the frustoconical shape. Examples of materials from which bands 162 can be made include, but are not limited to stretchable material having controlled stretch is an elastomeric nonwoven web. The elastomeric nonwoven web may be, for example, a spunbond web, a meltblown web, a bonded carded web, or a combination thereof. If the material is a web of meltblown fibers, it may include meltblown microfibers. The material may be made of elastomeric fiber forming polymers. Elastic polymers suitable for use in preparing the thermoplastic elastomeric fibers herein include without limitation diblock, triblock, or multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from the Shell Chemical Company, under the trade designation KRATON® elastomeric resin; polyurethanes, including those available from E.I. Du Pont de Nemours Co., under the trade name LYCRA® polyurethane; polyamides, including polyether block amides available from Ato Chemical Company, under the trade name PEBAX® polyether block amide; polyesters, such as those available from E.I. Du Pont de Nemours Co., under the trade name HYTREL® polyetherester; and single-site or metallocene-catalyzed polyolefins having density less than about 0.89 grams/cc, available from Dow Chemical Co. Under the trade name AFFINITY®.

Elastomeric meltblown webs may be produced using conventional meltblowing processes and apparatus as known in the art, for example as disclosed in U.S. Pat. No. 3,849,241 to Butin et al. In meltblowing, a thermoplastic resin, here an elastomeric resin, is fed into an extruder where it is melted and heated to an appropriate temperature required for fiber formation. The extruder feeds molten resin to a special meltblowing die. The resin emerges from the die orifices as molten threads into a high velocity stream of gas, usually air. The air attenuates the polymer into a blast of fine fibers which are collected on a moving screen placed in front of the blast. As the fibers land on the screen, they entangle to form a cohesive web.

Elastomeric spunbond webs employed in this invention may be formed by techniques known in the art, for example techniques described in U.S. Pat. No. 4,340,563 to Appel et al.; U.S. Pat. No. 3,692,618 to Dorschner et al.; and U.S. Pat. No. 3,802,817 to Matsuki et al. Examples of polymers which may be suitably used to form spunbond webs include the elastomeric polymers listed above. Other elasticated materials are known to persons skilled in the art and described with respect to elasticated materials or their equivalents in the following patent publications WO 2005037160; U.S. Pat. No. 6,465,073; WO 9316669; U.S. Pat. No. 6,248,097; EP 0556749B1; and EP 1201212, each of which is incorporated herein by reference in its entirety.

In the embodiment shown in FIG. 10, there are three (3) bands 162, but as would be apparent to those skilled in the art, more or less bands may be provided, as appropriate. The whole unitary frustoconical structure could be constructed of a single conically shaped band with or without nitinol (shape memory) reinforcing (supporting) structures. Mobile external coupling 160 is generally frustoconically shaped, such that bands 162 closer to body 107 have a larger diameter than bands 162 farther from body 107. Utilizing bands 162 of elasticated material for mobile external coupling 160 provides a good seal to a branch stent-graft and minimizes puckering of mobile external coupling 160 towards body 107, which may inhibit flow therethrough.

FIGS. 11-15 show an example of a delivery system that can be used to delivery stent-graft 100 to the target location within a vessel. FIG. 11 is a schematic partial cross-sectional view of a stent-graft delivery system 200 with stent-graft 100 disposed therein. Stent-graft delivery system 200 includes a tapered tip 202 that is flexible and able to provide trackability in tight and tortuous vessels. Other tip shapes such as bullet-shaped tips could also be used. The tip 202 includes a lumen 204 disposed therethrough for accommodating a first guidewire 220.

The tapered tip 202 includes a tapered outer surface 216 that gradually decreases in diameter in a distal direction. More particularly, tapered outer surface 216 has a first diameter at a proximal end and gradually decreases in diameter distally, i.e., in the direction away from the operator. Tapered outer surface 216 further includes a groove 218, as best seen in FIG. 12, for accommodating a second guidewire 222. A shoulder 212 reduces the diameter of a proximal portion of tip 202 to provide a sleeve landing surface 226. Shoulder 212 is generally annular and perpendicular to a longitudinal axis of stent-graft delivery system 200.

A first or outer sleeve 210 of stent-graft delivery system 200 extends over the outer cylindrical surface of sleeve landing surface 226 and abuts against shoulder 212 when the stent-graft delivery system 200 is in a pre-deployment configuration, as shown in FIG. 11. A second or inner sleeve 214 is disposed within outer sleeve 210. Inner sleeve 214 includes an opening through which mobile external coupling 120 extends, as described in more detail below.

Stent-graft delivery system 200 also includes an inner tube 205 that is coupled to a tip lumen 204 such that first guidewire 220 may extend the length of delivery system 200. Delivery system 200 may also include an outer tube 206 surrounding inner tube 205. A stop 208 is located at a distal end of stent-graft 100 when stent-graft 100 is loaded onto the delivery system 200. Stop 208 prevents longitudinal movement of stent-graft 100 as outer and inner sleeves 210, 214 are retracted or otherwise removed to release stent-graft 100. Stent-graft 100 is disposed within outer and inner sleeves 210, 214 in a compressed or delivery configuration wherein the diameter of stent-graft 100 is reduced such that it can be inserted through the vasculature.

Second guidewire 222 extends through stent-graft delivery system 200, through lumen 116 of stent-graft 100, through lumen 130 of mobile external coupling 120, between inner sleeve 214 and outer sleeve 210, and out a distal end of outer sleeve 210 through groove 218 of tip 202. A tube 224 may be provided to guide second guidewire 222 along this path and tube 224 may extend proximally to the proximal portion of delivery system 200. In the delivery or compressed configuration, mobile external coupling 120 may be folded proximally as shown schematically in FIGS. 11 and 13.

Outer sleeve 210 is a hollow tube and defines a lumen therein within which outer tube 206, inner tube 205, inner sleeve 214, and stent-graft 100 are disposed in the delivery configuration. Outer sleeve 210 is moved proximally, i.e. retracted, relative to outer tube 206 to release or deploy mobile external coupling 120. FIG. 14 shows outer sleeve 210 retracted and mobile external coupling 120 extended (deployed). After outer sleeve 210 is retracted, inner sleeve 214 is removed by, for example, a pull wire or other method known to those skilled in the art. A conventionally retracted inner sleeve 214 is not desirable because it would interfere with mobile external coupling 120. However, a pull string (not shown) to create a longitudinal slit to split inner sleeve 214 prior to retracting it may be used. Alternatively, a weakened (frangible) area (line) in inner sleeve 214 distal to mobile external coupling 120 may be utilized such that retracting inner sleeve 214 would cause the weakened area to split around mobile external coupling 120. Other means to accommodate mobile external coupling 120 when retracting inner sleeve 214 may be utilized, as would be apparent to those skilled in the art. Retracting inner sleeve 214 allows stent-graft 100 to deploy from its compressed configuration to its deployed or expanded configuration, as shown schematically in FIG. 15.

The stent-graft delivery system 200 described herein is only an example of a delivery system that can be used to delivery and deploy stent-graft 100 and many other delivery systems known to those skilled in the art could be utilized. For example, stent-graft 100 could be mounted onto a balloon to be expanded when at the target site. Other stent-graft-delivery systems, for example and not by way of limitation, the delivery systems described in U.S. Published Patent Application Publication Nos. 2008/0114442 and 2008/0262590 and U.S. Pat. No. 7,264,632, each of which is incorporated herein by reference in its entirety, may be utilized to deliver and deploy stent-graft 100. Further, although stent-graft delivery system 200 has been described with respect to stent-graft 100, delivery system 200 is equally suitable for use with stent-graft 150 (FIG. 10).

FIGS. 16-21 schematically show a method of delivering stent-graft 100 to a target site in a main vessel and a method of delivering a branch stent-graft to branch vessel. Although FIGS. 16-21 describe a method for delivering stent-graft 100, the method can be used to deliver stent-graft 150 (FIG. 10) as well. In the example described herein, the stent-graft 100 is delivered and deployed into the aorta 300. Portions of the aorta 300 include the ascending aorta 302, the aortic arch 304, and the descending aorta 306. Branching from the aortic arch are the brachiocephalic trunk 308, the left common carotid artery 314, and the left subclavian artery 316. The brachiocephalic trunk branches into the right subclavian artery 310 and the right common carotid artery 312. An aneurysm 318 in the area of the aortic arch 304 can be difficult to bypass or exclude with a stent-graft because blood flow to the branch arteries must be maintained.

In the embodiment shown in FIGS. 16-21, the aneurysm is sufficiently close to brachiocephalic trunk 308 that the stent-graft must extend between the brachiocephalic trunk 308 and the heart. In such a case and with a stent-graft 100 with only a single mobile external coupling 120, the mobile external coupling 120 is designed so as to be deployed into the brachiocephalic trunk 308 to perfuse the brachiocephalic trunk 308. Prior to the procedure for inserting stent-graft 100, bypass procedures installing bypass grafts or vessels (not shown) are performed to connect the right common carotid artery 312 to the left common carotid artery 314 and the left common carotid artery to the left subclavian artery 316. Such procedures may be performed one to two weeks prior to insertion of the stent-graft, and presents significantly less complications and risk than a surgical solution to repair an aneurysm 318 in the aortic arch. In this manner, maintaining perfusion to the brachiocephalic trunk 308, and hence the right common carotid artery 312, maintains perfusion to the left common carotid artery 314 and the left subclavian artery 316 Thus, the openings (or ostia) to these branch vessels directly from the aortic arch may be blocked by stent-graft 100. In the alternative, multiple mobile external couplings 120 may be provided in stent-graft 100. Further, if the aneurysm only affects the left common carotid artery 314 and the left subclavian artery 316, only one by-pass between the left common carotid artery 314 and the left subclavian artery needs to be performed, and then a stent-graft with a single mobile external coupling 120 can be utilized to perfuse the left common carotid artery 314. Alternatively, in such a situation, a stent-graft with two mobile external couplings may be provided, one for each of the branch vessels noted. Accordingly, while the embodiment of stent-graft 100 in the method described below includes a single mobile external coupling 120 and the mobile external coupling is deployed in the brachiocephalic trunk 308, those skilled in the art would recognize that multiple mobile external coupling can be used and the mobile external coupling(s) may be deployed in other branch arteries.

FIG. 16 shows the first guidewire 220 advanced from the descending aorta 306, through the aortic arch 304, and into the ascending aorta 302 and second guidewire 222 advanced from the descending aorta 306, through the aortic arch 304, and into brachiocephalic trunk 308. Guidewires 200, 222 are typically inserted into the femoral artery and routed up through the abdominal aorta, and into the thoracic aorta, as is known in the art.

FIG. 17 shows stent-graft delivery system 200, with stent-graft 100 compressed therein, advanced over guidewires 220, 222 to the target location in the aortic arch 304. The location of the stent-graft delivery system 200 and/or the stent-graft 100 may be verified radiographically and delivery system 200 and/or stent-graft 100 may include radiopaque markers as known in the art.

After stent-graft delivery system 200 is in the location where the mobile external coupling 120 of the stent graft 100 is approximately aligned with the opening into the branch vessel, outer sleeve 210 is retracted proximally to release mobile external coupling 120, as shown in FIG. 18. The shape memory fiber laced/weave construction of the mobile external coupling 120 provides a positive outward force that reduces the possibility of the mobile external coupling collapsing against body 107 after deployment. Delivery system 200 may then be moved to better align mobile external coupling with the branch artery, in this case, the brachiocephalic trunk 308. Further, due to the configuration of mobile external coupling 120, even if it is not perfectly aligned with brachiocephalic trunk 308, the top of the mobile external coupling 120 may move as it contacts and is being moved closers and closer and into the opening of the branch vessel to properly align it with brachiocephalic trunk 308 without having to move the entire stent-graft 100.

Figure 19:
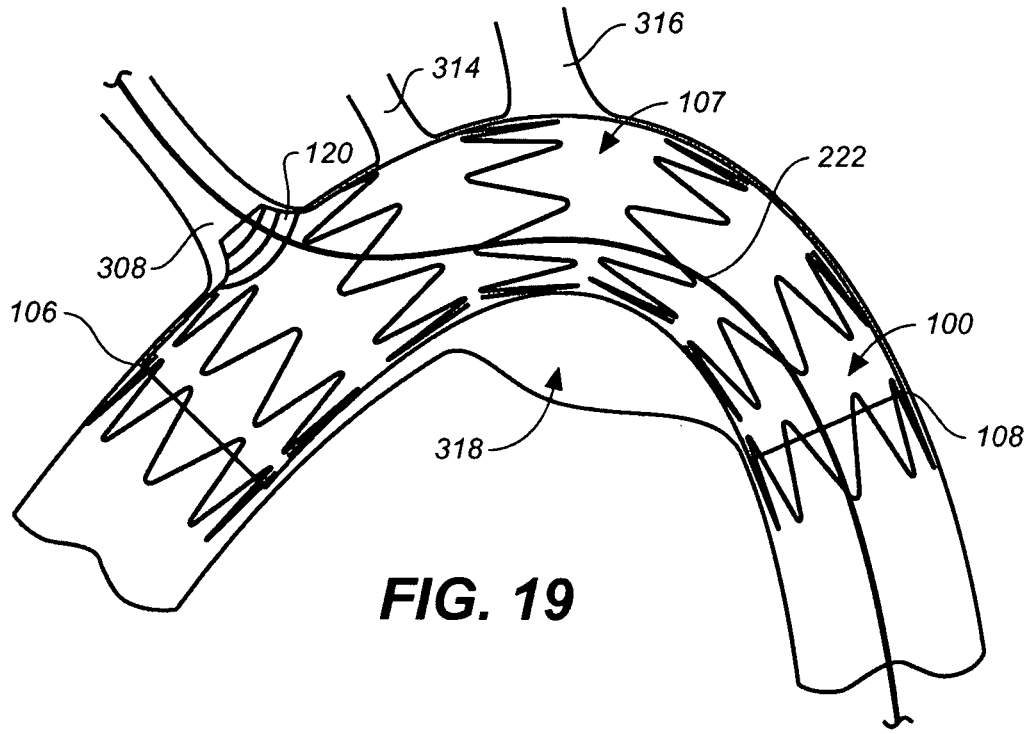
Figure 20:
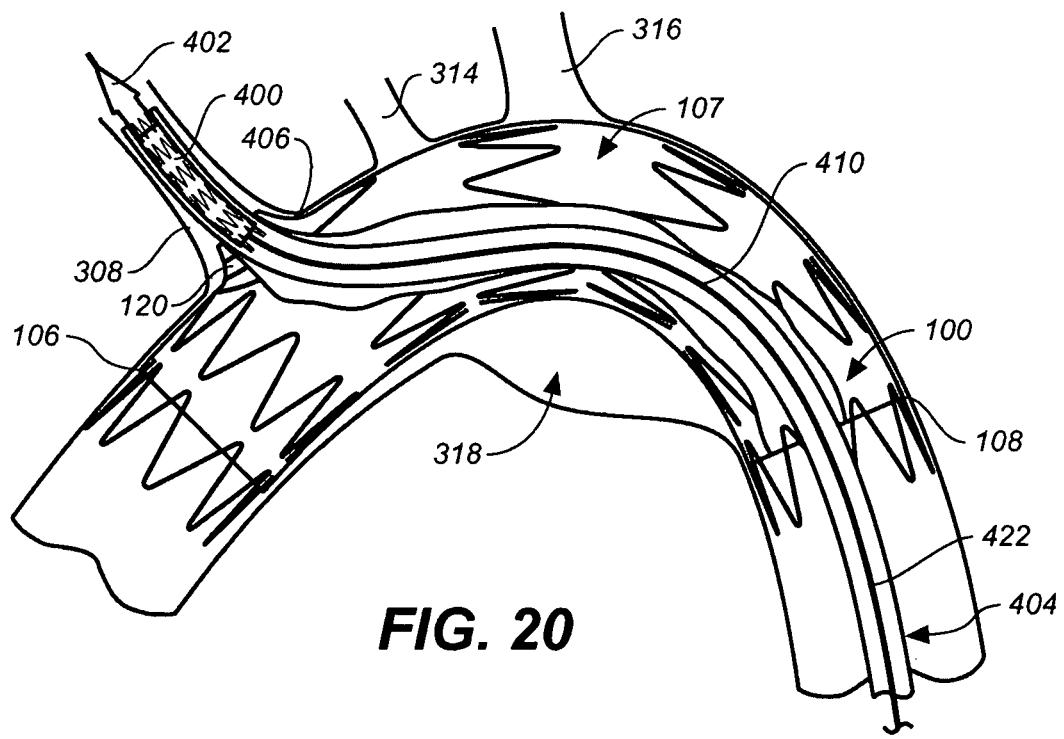
Figure 21:
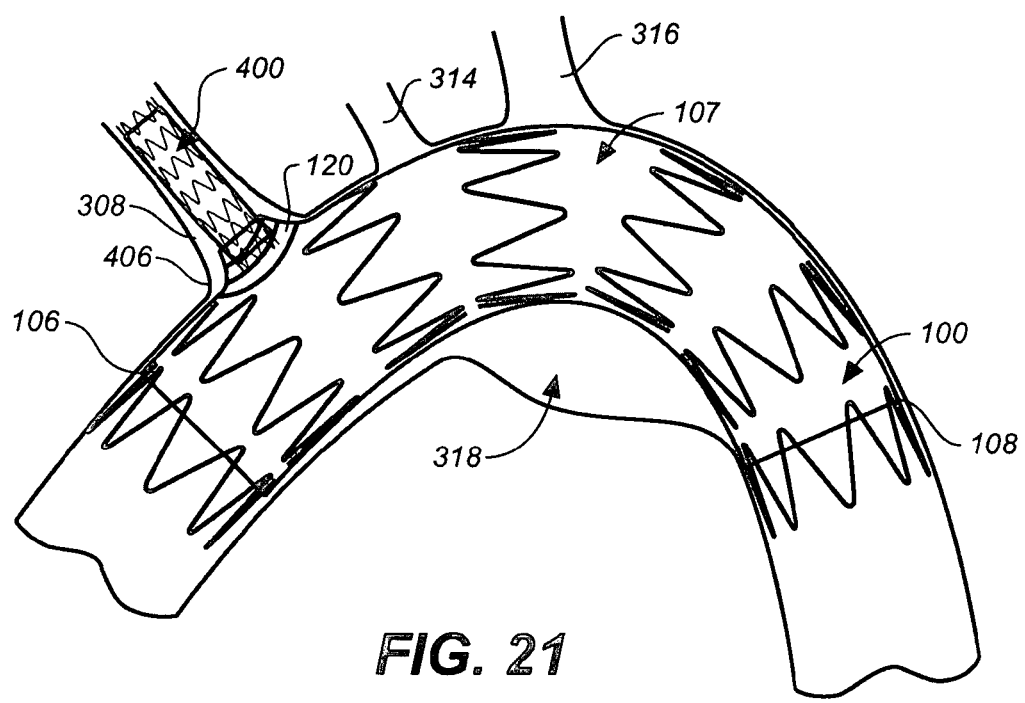

Once mobile external coupling 120 is deployed and in position in the brachiocephalic trunk 308, inner sleeve 214 may be retracted as explained above with respect to FIG. 15, thereby deploying the main body of the stent graft 100, as shown in FIG. 19. Once mobile external coupling 120 and stent-graft 100 are deployed, delivery system 200 may be removed. Second guidewire 222 may remain in place in brachiocephalic trunk 308 or may be replaced by another guidewire. A branch stent-graft delivery system 404 is advanced over second guidewire 222 and into brachiocephalic trunk 308, as shown in FIG. 20. Branch stent-graft delivery system includes a tip 402 and a sleeve (not shown), and contains therein a branch stent-graft 400. Branch stent-graft delivery system 404 and branch stent-graft 400 may be conventional. Branch stent-graft delivery system 404 is advanced into brachiocephalic trunk 308 such that a proximal portion 406 of branch stent-graft 400 remains inside of mobile external coupling 120. The sleeve constraining branch stent-graft 400 is then retracted proximally, thereby releasing branch stent-graft 400 from delivery system 404. The delivery system 404 is then withdrawn, as shown in FIG. 21. Because proximal portion 406 of branch stent-graft 400 is disposed within mobile external coupling 120 when branch stent-graft 400 is expanded, proximal portion 406 necks (narrows) at the top 126 of mobile external coupling 120 to conform with an inside surface of mobile external coupling 120.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. An endovascular prosthesis comprising:
a tubular body having a proximal end, a distal end, and a body lumen disposed between the proximal and distal ends, the tubular body including a body graft material and a plurality of stents coupled to the body graft material, the stents being generally coaxial with the tubular body; and
a mobile external coupling extending outwardly from the tubular body, wherein the mobile external coupling is generally frustoconically shaped and includes a base coupled to the tubular body, a top spaced from the tubular body, and a coupling lumen disposed between the base and the top, wherein the coupling lumen is in flow communication with the body lumen and wherein the mobile external coupling includes a coupling graft material, wherein the coupling graft material is a woven fabric with warp yarns which run generally parallel to a longitudinal axis of the mobile external coupling, the warp yarns including a shape memory material, wherein the shape memory material of the warp yarns is annealed straight to shape set the warp yarns to urge the mobile external coupling to protrude away from the tubular body.

2. The prosthesis of claim 1, wherein the shape memory material is a nickel-titanium alloy.

3. The prosthesis of claim 1, wherein the warp yarns are composite yarns made from combination of a thermoplastic yarns and the shape memory material.

4. The prosthesis of claim 1, wherein fill yarns of the mobile external coupling running generally transverse to the warp yarns are made from a thermoplastic yarn.

5. The prosthesis of claim 1, further comprising a separate ring disposed at the top of the mobile external coupling and coupled to the coupling graft material.

6. The prosthesis of claim 1, wherein a height of the mobile external coupling from the base to the top is in the range of 10-15 mm.

7. A main prosthesis and a branch prosthesis assembly comprising:
a main prosthesis configured for placement in a main vessel, the main prosthesis including a tubular body and a mobile external coupling, the tubular body having a proximal end, a distal end, a body lumen disposed between the proximal and distal ends, and a body graft material, the mobile external coupling extending outwardly from the tubular body and including a coupling lumen in flow communication with the body lumen, wherein the mobile external coupling includes a generally frustoconically shaped coupling graft material, wherein the coupling graft material is a woven fabric with warp yarns which run generally parallel to a longitudinal axis of the mobile external coupling, the warp yarns including a shape memory material, wherein the shape memory material of the warp yarns is annealed straight to shape set the warp yarns to urge the mobile external coupling to protrude away from the tubular body; and
a branch prosthesis configured for placement in a branch vessel that extends from the main vessel, the branch prosthesis including an outer surface in contact with an inner surface of the mobile external coupling;
wherein the mobile external coupling includes a base coupled to the tubular body and a top spaced from the tubular body, and wherein a distal portion of the mobile external coupling overlaps with a proximal end of the branch prosthesis.

8. The assembly of claim 7, wherein the shape memory material is a nickel-titanium alloy.

9. The assembly of claim 7, wherein the warp yarns are composite yarns made from combination of a thermoplastic yarns and the shape memory material.

10. The assembly of claim 7, wherein fill yarns of the mobile external coupling running generally transverse to the warp yarns are made from a thermoplastic yarn.

11. The assembly of claim 7, further comprising a separate ring disposed at the top of the mobile external coupling and coupled to the coupling graft material.

12. The assembly of claim 7, wherein a height of the mobile external coupling from the base to the top is in the range of 10-15 mm.

13. A method for excluding an aneurysm at a target location near a junction of a main vessel and a branch vessel, comprising the steps of:
delivering a main prosthesis in a compressed configuration to the target location in the main vessel, wherein the main prosthesis includes a tubular body and a mobile external coupling, the tubular body having a proximal end, a distal end, a body lumen disposed between the proximal and distal ends, and a body graft material, the mobile external coupling including a coupling graft material, wherein the coupling graft material is a woven fabric with warp yarns which run generally parallel to a longitudinal axis of the mobile external coupling, the warp yarns including a shape memory material, wherein the shape memory material of the warp yarns is annealed straight to shape set the warp yarns to urge the mobile external coupling to protrude away from the tubular body;
retracting a first sleeve to expose the mobile external coupling;
aligning the mobile external coupling with the branch vessel; and
deploying the tubular body such that the tubular body expands from the compressed configuration to an expanded configuration,
wherein the tubular body is disposed in the main vessel and the mobile external coupling extends into the branch vessel, wherein the mobile external coupling extends outwardly from the tubular body, and wherein the mobile external coupling includes a coupling lumen in flow communication with the body lumen.

14. The method of claim 13, further comprising the steps of:
delivering a branch vessel prosthesis in a compressed configuration to the branch vessel; and
deploying the branch vessel prosthesis such that the branch vessel prosthesis radially expands to an expanded configuration and an outside surface of a portion of the branch vessel prosthesis is in contact with an inner surface of a portion of the mobile external coupling.

15. The method of claim 13, wherein the mobile external coupling includes a base coupled to the tubular body and a top spaced from the tubular body.

16. The method of claim 15, wherein a height of the mobile external coupling from the base to the top is in the range of 10-15 mm.

17. The method of claim 15, further comprising a ring disposed at the top of the mobile external coupling.

18. The method of claim 15, wherein the base is generally elliptical in shape and the top is generally circular in shape.

19. The method of claim 18, wherein the base includes a major axis that is in the range of 20-30 mm and a minor axis that is in the range of 15-20 mm.

20. The method of claim 18, wherein the top includes a diameter in the range of 8-12 mm.

21. The method of claim 13, wherein the shape memory material is a nickel-titanium alloy.

22. The method of claim 13, wherein the warp yarns are composite yarns made from combination of a thermoplastic yarns and the shape memory material.

23. The method of claim 13, wherein fill yarns of the mobile external coupling running generally transverse to the warp yarns are made from a thermoplastic yarn.

24. The method of claim 13, wherein the main vessel is the aortic arch.

\* \* \* \* \*